United States Patent
Dyballa et al.

(10) Patent No.: US 9,517,986 B2
(45) Date of Patent: *Dec. 13, 2016

(54) PROCESS FOR PREPARING 2,2'-BIPHENOLS USING SELENIUM DIOXIDE

(71) Applicant: Evonik Degussa GmbH, Essen (DE)

(72) Inventors: Katrin Marie Dyballa, Recklinghausen (DE); Robert Franke, Marl (DE); Dirk Fridag, Haltern am See (DE); Siegfried R. Waldvogel, Gau-Algesheim (DE); Thomas Quell, Mainz (DE); Michael Mirion, Mainz (DE)

(73) Assignee: Evonik Degussa GmbH, Essen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/719,900

(22) Filed: May 22, 2015

(65) Prior Publication Data

US 2015/0336865 A1 Nov. 26, 2015

(30) Foreign Application Priority Data

May 26, 2014 (DE) ........................ 10 2014 209 967

(51) Int. Cl.
*C07C 37/11* (2006.01)
(52) U.S. Cl.
CPC ..................... *C07C 37/11* (2013.01)
(58) Field of Classification Search
None
See application file for complete search history.

(56) References Cited

U.S. PATENT DOCUMENTS

2008/0177113 A1* 7/2008 Bartsch ................... C07C 37/11
568/723

FOREIGN PATENT DOCUMENTS

WO   WO 2010/023258 A1   3/2010
WO   WO 2010/139687 A1   12/2010

OTHER PUBLICATIONS

Waitkins et al. ("Selenium Dioxide: Preparation, Properties, and use as Oxidizing Agent", Research Laboratories, Canadian Copper Refiners Limited, Montreal East, Quebec Canada, Feb. 1945, pp. 235-289).*
U.S. Appl. No. 14/720,063, filed May 22, 2015, Dyballa, et al.
U.S. Appl. No. 14/719,003, filed May 21, 2015, Dyballa, et al.
Giovanni Sartori, et al., "Selective Synthesis of Unsymmetrical Hydroxylated and Methoxylated Biaryls" J. Org. Chem., vol. 58, No. 25, 1993, pp. 7271-7273.
Extended European Search Report issued Oct. 12, 2015 in Patent Application No. 15168685.4 (with English translation of Categories of Cited Documents).
Bei-Sih Liao, et al., "Efficient oxidative coupling of 2,6-disubstituted phenol catalyzed by a dicopper(II) complex" Dalton Transactions, vol. 41, XP055143000, 2012, pp. 1158-1164.
Bernd Elsler, et al., "Metal- and Reagent-Free Highly Selective Anodic Cross-Coupling Reaction of Phenols" Angewandte Communications, Angew. Chem. Int. Ed., vol. 53, XP055203477, 2014, pp. 5210-5213.

* cited by examiner

*Primary Examiner* — Rosalynd Keys
(74) *Attorney, Agent, or Firm* — Oblon, McClelland, Maier & Neustadt, L.L.P.

(57) ABSTRACT

A process for preparing a 2,2'-biphenol, proceeds by a) adding a first phenol to a reaction mixture, b) adding a second phenol to the reaction mixture, c) adding selenium dioxide to the reaction mixture, d) adding an acid having a pKa in the range from 0.0 to 5.0 to the reaction mixture, and e) heating the reaction mixture such that the first phenol and the second phenol are converted to said 2,2'-biphenol.

14 Claims, No Drawings

PROCESS FOR PREPARING 2,2'-BIPHENOLS USING SELENIUM DIOXIDE

BACKGROUND OF THE INVENTION

1. Field of the Invention

The invention relates to a process for preparing 2,2'-biphenol using selenium dioxide.

2. Discussion of the Background

The direct coupling of phenols to give the corresponding biphenol derivatives which are of great industrial interest continues to be a challenge since these reactions are often neither regio- nor chemoselective.

The term "phenols" is used as a generic term in this application and therefore also encompasses substituted phenols.

One possible way of synthesizing these biphenols is by means of electrochemical processes. In this case, carbon electrodes such as graphite, glassy carbon, BDD or transition metals such as platinum are used (cf. F. Stecker, A. Fischer, I. M. Malkowsky, S. R. Waldvogel, A. Kirste, WO 2010139687 A1 and A. Fischer, I. M. Malkowsky, F. Stecker, S. R. Waldvogel, A. Kirste WO 2010023258 A1). A disadvantage of these electrochemical methods is the cost of some of the apparatus, which has to be manufactured specially. Moreover, scale-up to the ton scale, as is typically required in industry, is sometimes very complex and in some cases even impossible.

Direct cross-coupling of unprotected phenol derivatives under conventional organic conditions has been possible only in a few examples to date. For this purpose, usually superstoichiometric amounts of inorganic oxidizing agents such as $AlCl_3$, $FeCl_3$, $MnO_2$, or DDQ, which is organic, are used (cf. G. Sartori, R. Maggi, F. Bigi, M. Grandi, J. Org. Chem. 1993, 58, 7271).

Alternatively, such coupling reactions are conducted in a multistage sequence. In this case, leaving functionalities and often toxic, conjugated transition metal catalysts based on palladium, for example, are used.

A great disadvantage of the abovementioned methods for phenol coupling is the need for dry solvents and for exclusion of air. Both mean a high level of complexity, specifically when the process is to be used on the industrial scale.

Furthermore, the reactions described in the related art often give rise to toxic by-products which have to be removed from the desired product in a complex manner and disposed of at great cost. The increasing scarcity of raw materials (for example boron and bromine) and the rising relevance of environmental protection is increasing the cost of such transformations. Particularly in the case of utilization of multistage syntheses, an exchange of various solvents is necessary, which constitutes a high level of complexity and is an additional cost factor.

SUMMARY OF THE INVENTION

It was an object of the invention to provide a process which does not have the disadvantages described in connection with the related art. More particularly, a process by which 2,2'-biphenols can be prepared selectively is to be provided, i.e. one in which the preparation gives rise to a minimum amount of by-products. The process should also be usable on the industrial scale.

This and other objects are achieved by a process for preparing a 2,2'-biphenol, comprising:
  a) adding a first phenol to a reaction mixture,
  b) adding a second phenol to the reaction mixture,
  c) adding selenium dioxide to the reaction mixture,
  d) adding an acid having a pKa in the range from 0.0 to 5.0 to the reaction mixture, and
  e) heating the reaction mixture such that the first phenol and the second phenol are converted to said 2,2'-biphenol.

DETAILED DESCRIPTION OF THE INVENTION

Any ranges mentioned below include all values and subvalues between the lower and upper limits of the range.

The present invention provides a process for preparing 2,2'-biphenols, comprising the process steps of:
  a) adding a first phenol to the reaction mixture,
  b) adding a second phenol to the reaction mixture,
  c) adding selenium dioxide to the reaction mixture,
  d) adding an acid having a pKa in the range from 0.0 to 5.0 to the reaction mixture,
  e) heating the reaction mixture such that the first phenol and the second phenol are converted to a 2,2'-biphenol.
Steps a) to d) can be conducted here in any sequence.

The process is not limited to the components detailed above. Further constituents, for example solvents, may likewise be present in the reaction mixture.

If the acid has more than one pKa, the $pKa_1$ should be considered. In the case of the invention, this has to be in the range from 0.0 to 5.0. The pKa is a value for the molecule as present under neutral (i.e. neither acidic nor basic) conditions, and not the value for the corresponding acid (pKca). Thus, in a neutral environment, pyridine, for example, should be regarded as non-protonated. The definition of the pKa and pKb is sufficiently well known to those skilled in the art and can be found in the corresponding technical literature.

A problem with the use of selenium dioxide is that the corresponding 2,2'-selenobiaryl ether and the corresponding Pummerer ketone can be obtained as by-products in large amounts. In the case of an unfavourable reaction regime, it may even be the case that the 2,2'-selenobiaryl ether is the main product of the reaction. According to the objective of the invention, the aim, however, is to conduct the reaction specifically in such a way that the level of such by-products is reduced to a minimum.

Through addition of selenium dioxide as oxidizing agent, depending on the reaction conditions, 2,2'-biphenols or 2,2'-selenobiaryl ethers can be obtained as main products of the reaction (cf. Scheme 1).

Scheme 1:

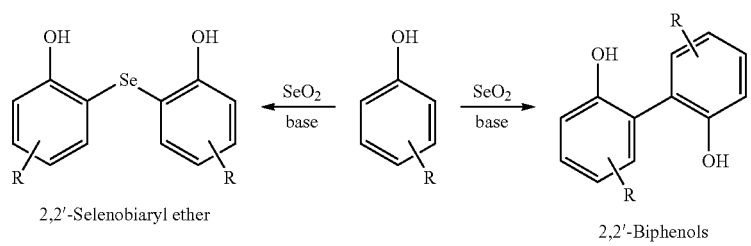

2,2'-Selenobiaryl ether 2,2'-Biphenols

It has been found that the reaction can be shifted in a controlled manner in the direction of the 2,2'-biphenols through addition of an acid having a pKa in the range from 0.0 to 5.0.

Further advantages over the processes described in the related art are that it is not necessary to work with exclusion of moisture or oxygen. This constitutes a distinct advantage over other synthesis routes. This direct method of C—C coupling is an efficient and selective process which stands out advantageously from the existing multistage synthesis routes.

The reaction can be steered in the direction of C—C coupling by means of the pKa values. As a result of predominant formation of the desired main product and reduction in the formation of higher molecular weight overoxidation products, the workup is distinctly simplified.

Unconverted reactants and solvents used can be recovered by distillation and used for further reactions. Thus, the process according to the invention fulfils the requirements for an economic industrial scale process.

Moreover, selenium dioxide is used in the process according to the invention. Selenium dioxide is a waste product from metal purification and ore refining. Thus, in the process claimed here, a waste product from other processes is reused with addition of value. This is an important topic especially against the background of the sustainability of processes.

In one variant of the process, the first phenol in process step a) is a compound of the general formula I:

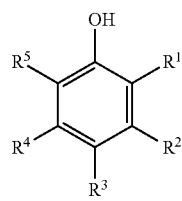

I where $R^1$, $R^2$, $R^3$, $R^4$, $R^5$ are each independently selected from:

—H, —$(C_1-C_{12})$-alkyl, —O—$(C_1-C_{12})$-alkyl, —$(C_6-C_{20})$-aryl, —O—$(C_6-C_{20})$-aryl, -halogen (such as Cl, F, Br, I), —OC=O—$(C_1-C_{12})$-alkyl, two adjacent radicals may additionally be joined to one another to form a condensed system, where the alkyl and aryl groups mentioned may be substituted, and at least $R^1$ or $R^5$ is —H.

$(C_1-C_{12})$-Alkyl and O—$(C_1-C_{12})$-alkyl may each be unsubstituted or substituted by one or more identical or different radicals selected from:

$(C_3-C_{12})$-cycloalkyl, $(C_3-C_{12})$-heterocycloalkyl, $(C_6-C_{20})$-aryl, fluorine, chlorine, cyano, formyl, acyl or alkoxycarbonyl.

$(C_6-C_{20})$-Aryl and O—$(C_6-C_{20})$-aryl may each be unsubstituted or substituted by one or more identical or different radicals selected from:

—H, —$(C_1-C_{12})$-alkyl, —O—$(C_1-C_{12})$-alkyl, —O—$(C_6-C_{20})$-aryl, —$(C_6-C_{20})$-aryl, -halogen (such as Cl, F, Br, I), —COO—$(C_1-C_{12})$-alkyl, —CONH—$(C_1-C_{12})$-alkyl, —$(C_6-C_{20})$-aryl-CON[$(C_1-C_{12})$-alkyl]$_2$, —CO—$(C_1-C_{12})$-alkyl, —CO—$(C_6-C_{20})$-aryl, —COOH, —OH, —SO$_3$H, —SO$_3$Na, —NO$_2$, —CN, —NH$_2$, —N[$(C_1-C_{12})$-alkyl]$_2$.

In the context of the invention, the expression $(C_1-C_{12})$-alkyl encompasses straight-chain and branched alkyl groups.

Preferably, these groups are unsubstituted straight-chain or branched $(C_1-C_8)$-alkyl groups and most preferably $(C_1-C_6)$-alkyl groups. Examples of $(C_1-C_{12})$-alkyl groups are especially methyl, ethyl, propyl, isopropyl, n-butyl, isobutyl, sec-butyl, tert-butyl, n-pentyl, 2-pentyl, 2-methylbutyl, 3-methylbutyl, 1,2-dimethylpropyl, 1,1-dimethylpropyl, 2,2-dimethylpropyl, 1-ethylpropyl, n-hexyl, 2-hexyl, 2-methylpentyl, 3-methylpentyl, 4-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1,1,2-trimethylpropyl, 1,2,2-trimethylpropyl, 1-ethylbutyl, 1-ethyl-2-methylpropyl, n-heptyl, 2-heptyl, 3-heptyl, 2-ethylpentyl, 1-propylbutyl, n-octyl, 2-ethylhexyl, 2-propylheptyl, nonyl, decyl.

The elucidations relating to the expression —$(C_1-C_{12})$-alkyl also apply to the alkyl groups in —O—$(C_1-C_{12})$-alkyl, i.e. in —$(C_1-C_{12})$-alkoxy. Preferably, these groups are unsubstituted straight-chain or branched —$(C_1-C_6)$-alkoxy groups.

Substituted $(C_1-C_{12})$-alkyl groups and substituted $(C_1-C_{12})$-alkoxy groups may have one or more substituents, depending on their chain length. The substituents are preferably each independently selected from:

—$(C_3-C_{12})$-cycloalkyl, —$(C_3-C_{12})$-heterocycloalkyl, —$(C_6-C_{20})$-aryl, fluorine, chlorine, cyano, formyl, acyl or alkoxycarbonyl.

In one variant of the process, $R^1$, $R^2$, $R^3$, $R^4$, $R^5$ are each independently selected from:

—H, —$(C_1-C_{12})$-alkyl, —O—$(C_1-C_{12})$-alkyl, —$(C_6-C_{20})$-aryl, —O—$(C_6-C_{20})$-aryl, where the alkyl and aryl groups mentioned may be substituted, and at least $R^1$ or $R^5$ is —H.

In one variant of the process, $R^1$, $R^2$, $R^3$, $R^4$, $R^5$ are each independently selected from:

—H, —$(C_1-C_{12})$-alkyl, where the alkyl and aryl groups mentioned may be substituted, and at least $R^1$ or $R^5$ is —H.

In one variant of the process, $R^1$, $R^3$, $R^5$ are each independently selected from:

—H, —$(C_1-C_{12})$-alkyl, where the alkyl groups mentioned may be substituted, and at least $R^1$ or $R^5$ is —H.

In one variant of the process, $R^2$ and $R^4$ are each —H.

In one variant of the process, the second phenol in process step b) is a compound of the general formula II:

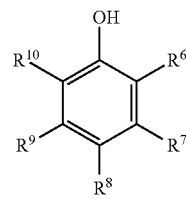

II where $R^6$, $R^7$, $R^8$, $R^9$, $R^{10}$ are each independently selected from:

—H, —$(C_1-C_{12})$-alkyl, —O—$(C_1-C_{12})$-alkyl, —$(C_6-C_{20})$-aryl, —O—$(C_6-C_{20})$-aryl, -halogen (such as Cl, F, Br, I), —OC=O—$(C_1-C_{12})$-alkyl, two adjacent radicals may additionally be joined to one another to form a condensed system, where the alkyl and aryl groups mentioned may be substituted, and at least $R^6$ or $R^{10}$ is —H.

In one variant of the process, $R^6$, $R^7$, $R^8$, $R^9$, $R^{10}$ are each independently selected from:

—H, —($C_1$-$C_{12}$)-alkyl, —O—($C_1$-$C_{12}$)-alkyl, —($C_6$-$C_{20}$)-aryl, —O—($C_6$-$C_{20}$)-aryl, where the alkyl and aryl groups mentioned may be substituted, and at least $R^6$ or $R^{10}$ is —H.

In one variant of the process, $R^6$, $R^7$, $R^8$, $R^9$, $R^{10}$ are each independently selected from:

—H, —($C_1$-$C_{12}$)-alkyl, where the alkyl and aryl groups mentioned may be substituted, and at least $R^6$ or $R^{10}$ is —H.

In one variant of the process, $R^6$, $R^8$, $R^{10}$ are each independently selected from:

—H, —($C_1$-$C_{12}$)-alkyl, where the alkyl groups mentioned may be substituted, and at least $R^6$ or $R^{10}$ is —H.

In one variant of the process, $R^7$ and $R^9$ are each —H.

In one variant of the process, the first phenol corresponds to the second phenol.

This variant is thus a homo-coupling of two identical phenols. Ortho-ortho coupling thus gives rise to the desired 2,2'-biphenols.

In one variant of the process, the selenium dioxide is added in process step c) in a molar ratio based on the sum total of the first and second phenols within a range from 0.25 to 1.2.

Preference is given here to the range from 0.25 to 0.9, and particular preference to the range from 0.4 to 0.7.

The fact that the selenium dioxide can be used in a substoichiometric amount is a further advantage over the reaction described in the related art with other inorganic oxidizing agents, for example $AlCl_3$, $FeCl_3$ or $MnO_2$.

In one variant of the process, the acid in process step d) is selected from: acetic acid (pKa 4.8), formic acid (pKa 3.8), trifluoroacetic acid (pKa 0.23), propionic acid (pKa 4.9), phosphoric acid ($pKa_1$ 2.1).

In one variant of the process, the acid is used as solvent in process step d).

In one variant of the process, the reaction mixture is heated in process step e) to a temperature in the range from 50° C. to 110° C.

Preference is given here to the range from 60° C. to 100° C., and particular preference to the range from 70° C. to 90° C.

The temperatures specified here are the temperatures measured in the oil bath.

In one variant of the process, the heating is effected in process step e) over a period in the range from 5 minutes to 24 hours.

Preference is given here to the range from 15 minutes to 2.5 hours, and particular preference to the range from 15 minutes to 2.0 hours.

Having generally described this invention, a further understanding can be obtained by reference to certain specific examples which are provided herein for purposes of illustration only, and are not intended to be limiting unless otherwise specified.

EXAMPLES

Analysis

NMR spectroscopy

The mass spectroscopy studies were conducted on multinucleus resonance spectrometers of the AC 300 or AV II 400 type from Bruker, Analytische Messtechnik, Karlsruhe. The solvent used was $CDCl_3$. The $^1H$ and $^{13}C$ spectra were calibrated according to the residual content of undeuterated solvent using the NMR Solvent Data Chart from Cambridge Isotopes Laboratories, USA. Some of the $^1H$ and $^{13}C$ signals were assigned with the aid of H,H-COSY, H,H-NOESY, H,C-HSQC and H,C-HMBC spectra. The chemical shifts are reported as δ values in ppm. For the multiplicities of the NMR signals, the following abbreviations were used: s (singlet), bs (broad singlet), d (doublet), t (triplet), q (quartet), m (multiplet), dd (doublet of doublets), dt (doublet of triplets), tq (triplet of quartets). All coupling constants J were reported in hertz (Hz) together with the number of bonds covered. The numbering given in the assignment of signals corresponds to the numbering shown in the formula schemes, which do not necessarily have to correspond to IUPAC nomenclature.

General Procedure 8.2 mmol of the particular phenol are dissolved in the appropriate solvent (8.2 M). The reaction mixture is heated, and 4.9 mmol of selenium dioxide are added while stirring. The solvent is distilled under reduced pressure (temperature<70° C.). A frit is prepared with 2.5 cm of silica gel (at the bottom) and 2.5 cm of zeolite (at the top). The distillation residue is taken up in the eluent and applied to the filtration column. Cyclohexane:ethyl acetate (95:5) is used to wash the product off the frit and collect it in fractions. The fractions containing product are combined and freed of the eluent by distillation.

The fractions obtained are recrystallized from 95:5 cyclohexane:ethyl acetate. For this purpose, the solid residue is dissolved at 50° C., and insoluble residues are filtered off using a glass frit. The reaction product crystallizes out of the saturated solution at room temperature overnight. The resulting crystals are washed once again with cold cyclohexane.

The structural formula shows the main product obtained in each reaction.

3,3',5,5'-Tetramethylbiphenyl-2,2'-diol

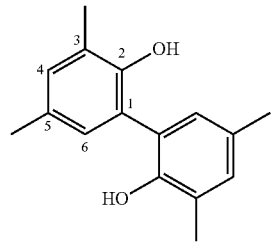

The reaction is conducted according to the general procedure in a screw-top test tube. For this purpose, 1.00 g (8.2 mmol, 1.0 equiv.) of 2,4-dimethylphenol and 0.54 g (4.9 mmol, 0.6 equiv.) of selenium dioxide are dissolved and heated in 1 ml of acid. The product is obtained as a beige crystalline solid.

$^1H$ NMR (300 MHz, $CDCl_3$):

δ (ppm)=7.00 (s, 2H, 6-H), 6.87 (s, 2H, 4-H), 5.07 (s, 2H, OH), 2.27 (s, 12H, 3-$CH_3$, 5-$CH_3$).

$^{13}C$ NMR (75 MHz, $CDCl_3$):

δ (ppm)=149.2 (C-2), 132.1 (C-4), 130.0 (C-5), 128.5 (C-6), 125.1 (C-3), 122.1 (C-1), 20.4 (5-$CH_3$), 16.2 (3-$CH_3$).

Bis(3,5-dimethyl-2-hydroxyphenyl)selenium

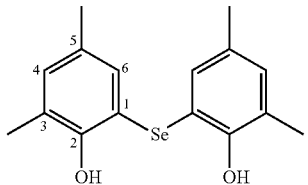

The reaction is conducted according to the general procedure in a screw-top test tube. For this purpose, 1.00 g (8.2 mmol, 1.0 equiv.) of 2,4-dimethylphenol and 0.54 g (4.9 mmol, 0.6 equiv.) of selenium dioxide are dissolved and heated in 1 ml of pyridine. The product is obtained as a colourless crystalline solid.

$^1$H NMR (400 MHz, CDCl$_3$):
δ (ppm)=7.12 (s, 2H, 6-H), 6.91 (s, 2H, 4-H), 5.97 (s, 2H, OH), 2.23 (s, 6H, 3-CH$_3$) 2.23 (s, 6H, 5-CH$_3$).
$^{13}$C NMR (100 MHz, CDCl$_3$):
δ (ppm)=151.7 (C-2), 133.2 (C-3), 133.1 (C-5), 130.4 (C-4), 124.2 (C-6), 114.9 (C-1), 20.3 (5-CH$_3$), 16.5 (3-CH$_3$).
$^{77}$Se NMR (76 MHz, CDCl$_3$):
δ (ppm)=163.36 ppm.

Bis(3-tert-butyl-5-methyl-2-hydroxyphenyl)selenium

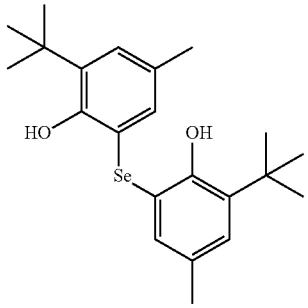 [SMILES: Cc1cc([Se]c2cc(C)cc(C(C)(C)C)c2O)c(O)c(C(C)(C)C)c1]

The reaction is conducted according to the general procedure in a screw-top test tube. For this purpose, 1.32 g (8.0 mmol, 1.0 equiv.) of 2-tert-butyl-4-methylphenol and 0.54 g (4.9 mmol, 0.6 equiv.) of selenium dioxide were dissolved and heated in 1 ml of pyridine.

$^1$H NMR (300 MHz, CDCl$_3$):
δ (ppm)=7.15 (s, 2H, 6-H), 7.05 (s, 2H, 4-H), 5.07 (s, 2H, OH), 2.21 (s, 6H, 5-CH$_3$), 2.21 (s, 18H, 3-C(CH$_3$)$_3$.
$^{13}$C NMR (75 MHz, CDCl$_3$):
δ (ppm)=152.1, 136.4, 133.4, 120.1, 129.5, 117.2, 35.1, 29.6, 20.8.

3,3'-Di-tert-butyl,5,5'-dimethylbiphenyl-2,2'-diol

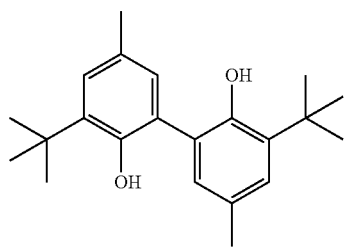 [SMILES: Cc1cc(-c2cc(C)cc(C(C)(C)C)c2O)c(O)c(C(C)(C)C)c1]

The reaction is conducted according to the general procedure in a screw-top test tube. For this purpose, 5.00 g (30.5 mmol, 1.0 equiv.) of 2-tert-butyl-4-methylphenol and 2.03 g (18.3 mmol, 0.6 equiv.) of selenium dioxide were dissolved and heated in 5 ml of acetic acid.

$^1$H NMR (400 MHz, CDCl$_3$):
δ (ppm)=7.17 (d, J=2.2 Hz, 2H), 6.91 (d, J=2.2 Hz, 2H), 5.19 (s, 2H), 2.33 (s, 6H), 1.45 (s, 18H).
$^{13}$C NMR (75 MHz, CDCl$_3$):
δ (ppm)=149.9, 137.0, 129.7, 128.9, 128.6, 122.7, 35.0, 29.8, 27.0.

Bis(3,5-Di-tert-butyl-2-hydroxyphenyl)selenium

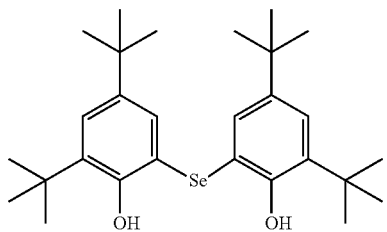 [SMILES: CC(C)(C)c1cc([Se]c2cc(C(C)(C)C)cc(C(C)(C)C)c2O)c(O)c(C(C)(C)C)c1]

$^1$H NMR (400 MHz, CDCl$_3$):
δ (ppm)=7.31 (d, J=2.4 Hz, 2H), 7.29 (d, J=2.4), 6.29 (s, 2H), 1.42 (s, 18H), 1.24 (s, 18H).
$^{13}$C NMR (75 MHz, CDCl$_3$):
δ (ppm)=151.7, 143.5, 135.8, 129.8, 125.6, 117.2, 35.4, 34.4, 31.6, 29.7.

3,3',5,5'-Tetra-tert-butylbiphenyl-2,2'-diol

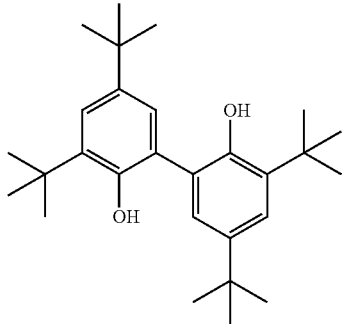 [SMILES: CC(C)(C)c1cc(-c2cc(C(C)(C)C)cc(C(C)(C)C)c2O)c(O)c(C(C)(C)C)c1]

In a 100 ml round-bottom flask, 9.700 g of 2,4-di-tert-butylphenol (47 mmol) were dissolved in 65 ml of acetic acid, 3.130 g of selenium dioxide (28 mmol) were added and the mixture was heated in an oil bath at 100° C. After 30 minutes, the reaction was ended, diluted with 250 ml of ethyl acetate and filtered. The filtrate was washed three times with 150 ml each time of water, and the organic phase was removed, dried over magnesium sulphate and freed of the solvent. The crude product was purified by means of column chromatography: the length of the column was 8 cm with a diameter of 12 cm. The eluent used was cyclohexane/ethyl acetate in a ratio of 99/1. The product thus obtained was heated under reflux in 90 ml of heptane until it dissolved completely. The solution was cooled down to room temperature in an oil bath overnight. The product thus obtained was filtered off and washed with cold heptane. The filtrate was concentrated under reduced pressure and crystallized at 4° C. in a refrigerator for three days. Colourless needles were obtained.

Yield: 5.459 g (13.3 mmol), 56%

$^1$H NMR (400 MHz, CDCl$_3$): δ (ppm)=7.39 (d, J=2.4 Hz, 2H), 7.11 (d, J=2.4, 2H), 5.21 (s, 2H), 1.45 (s, 18H), 1.32 (s, 18H).

$^{13}$C NMR (75 MHz, CDCl$_3$): δ (ppm)=149.9, 143.0, 125.4, 124.9, 122.4, 35.4, 34.6, 31.7, 29.8.

3,3'-Diisopropyl-5,5',6,6'-tetramethyl-2,2'-biphenol

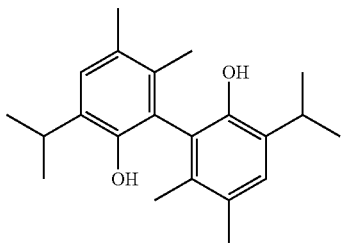 [SMILES: Cc1cc(C(C)C)c(O)c(-c2c(C)c(C)cc(C(C)C)c2O)c1C]

In a 50 ml round-bottom flask, 860 mg of 4,5-dimethyl-2-isopropylphenol (5 mmol) were dissolved in 20 ml of acetic acid, 581 mg of selenium dioxide (5 mmol) were added and the mixture was heated in an oil bath at 105° C. After 40 minutes, the reaction was ended, diluted with 100 ml of ethyl acetate and filtered. The filtrate was washed three times with 50 ml each time of water, and the organic phase was removed and dried over magnesium sulphate. 872 mg of crude product were obtained, which were purified by means of Kugelrohr distillation, in which the product sublimed at 0.001 mbar and 74° C. 351 mg of colourless clear crystals were obtained. In spite of increasing temperature, it was not possible to sublime the product completely, and so the gas chromatogram of the distillation bottoms showed minor traces of the product. For product preparation, the respective samples are filtered as well through a Pasteur pipette filled with silica gel (about 4 cm). The majority of the distillation bottoms remained stuck to the silica gel.

Yield: 351 mg (1.0 mmol), 41%

$^1$H NMR: (400 MHz, CDCl$_3$) δ [ppm]=1.25 (dd, 12H), 1.85 (s, 6H), 2.26 (s, 6H), 3.26 (hept, J=6.9 Hz, 2H), 4.60 (s, 2H), 7.06 (s, 2H);

$^{13}$C NMR: (100 MHz, CDCl$_3$) δ [ppm]=16.21, 20.11, 22.72, 22.87, 27.19, 120.34, 128.24, 128.74, 132.12, 133.81, 149.04;

Melting range: 108.8-109.7° C.

3,3'-Di-tert-butyl-5,5',6,6'-tetramethyl-2,2'-biphenol

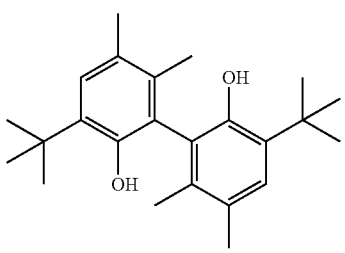 [SMILES: Cc1cc(C(C)(C)C)c(O)c(-c2c(C)c(C)cc(C(C)(C)C)c2O)c1C]

In a 100 ml round-bottom flask, 10.719 g of 2-tert-butyl-4,5-dimethylphenol (60 mmol) were dissolved in 35 ml of acetic acid, 4.003 g of selenium dioxide (36 mmol) were added and the mixture was heated in an oil bath at 80° C. After 75 minutes, the reaction was ended, diluted with 250 ml of ethyl acetate and filtered. The filtrate was washed three times with 150 ml each time of water, and the organic phase was removed and dried over magnesium sulphate. The crude product was filtered through a layer composed of 3 cm of silica gel and 2 cm of Celite, using a 95/5 mixture of cyclohexane/ethyl acetate as eluent. The filtrate was freed of the solvent and heated under reflux in heptane. Gradual cooling to room temperature overnight led to clear, pale yellowish needles. The product was filtered off and washed with cold heptane. The filtrate was concentrated to half the volume and crystallized at 4° C. over the course of two days.

Yield: 5.004 g (14.1 mmol), 47%

$^1$H NMR: (400 MHz, CDCl$_3$) δ [ppm]=1.40 (s, 18H), 1.83 (s, 6H), 2.26 (s, 6H), 4.81 (s, 2H), 7.14 (s 2H);

Melting range: 165.2-165.5° C.

3,3',5,5',6,6'-Hexamethyl-2,2'-biphenol

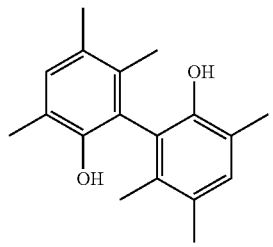

In a 10 ml round-bottom flask, 512 mg of 2,4,5-trimethylphenol (4 mmol) were dissolved in 5 ml of acetic acid, 229 mg of selenium dioxide (2 mmol) were added and the mixture was heated in an oil bath at 80° C. After 120 minutes, the reaction was ended, diluted with 50 ml of dichloromethane and filtered. The filtrate was washed three times with 50 ml each time of water, and the organic phase was removed, dried over magnesium sulphate and freed of the solvent. The crude product was purified by column chromatography: the column length was 10 cm and the column diameter 3 cm. An eluent composed of 95/5 cyclohexane/ethyl acetate was used. The purified product was dissolved at 60° C. in 5 ml of heptane. Crystallization at 4° C. gave colourless acicular crystals after two days. The product was filtered off, washed with cold heptane and freed of solvent residues under reduced pressure.

Yield: 226 mg (0.8 mmol), 47%

$^1$H NMR: (400 MHz, CDCl$_3$) δ [ppm]=1.40 (s, 18H), 1.83 (s, 6H), 2.26 (s, 6H), 4.81 (s, 2H), 7.14 (s 2H);

$^{13}$C NMR: (75 MHz, CDCl$_3$) δ [ppm]=15.73, 16.07, 19.51, 119.96, 121.38, 128.48, 132.67, 133.87, 149.79

Melting range: 68.8-169.5° C.

The results of the above-described reaction, and variations thereof, are shown in the tables which follow. The processes according to the invention are identified here by *.

The following compound classes are specified in detail in the tables:

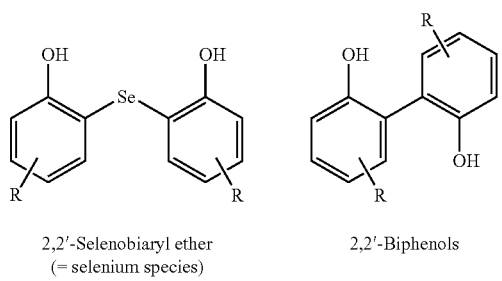

2,2'-Selenobiaryl ether (= selenium species)     2,2'-Biphenols

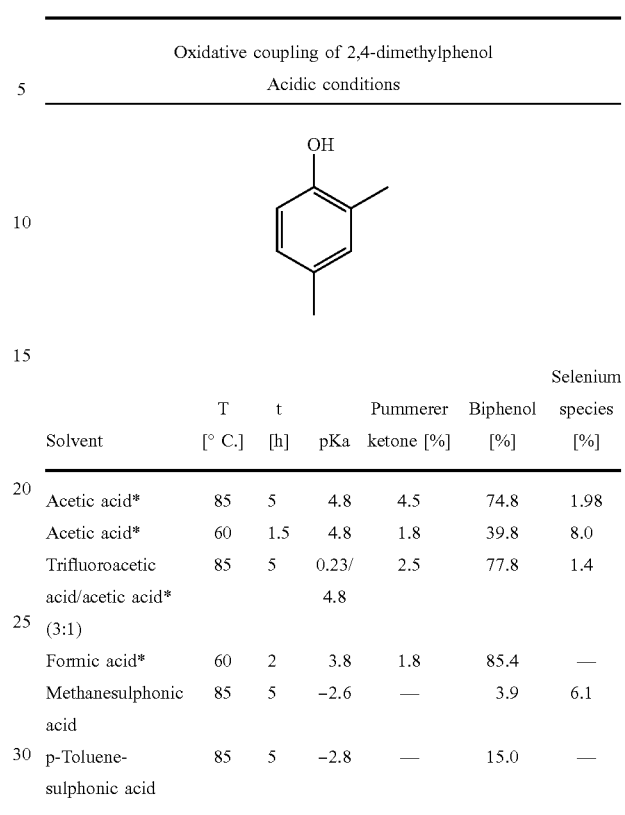

Pummerer ketone

TABLE 1a

Oxidative coupling of 2,4-dimethylphenol
Basic conditions

| Solvent | T [° C.] | t [h] | pKb | Pummerer ketone [%] | Biphenol [%] | Selenium species [%] |
|---|---|---|---|---|---|---|
| Pyridine | 60 | 5 | 8.9 | — | — | 79.1 |
| Pyridine | 85 | 5 | 8.9 | 2.6 | 13.1 | 59.6 |
| Pyridine | 100 | 0.5 | 8.9 | 1.9 | 11.0 | 39.9 |
| Triethylamine (dry) | 80 | 4 | 3.3 | — | — | 1.8 |
| DMF | 85 | 5 | −1.1 | 4.2 | 19.1 | 18.8 |

It can be inferred from Table 1a that (with the exception of dimethylformamide (DMF)), the desired biphenol is obtained only as a by-product. In the case of DMF, the biphenol and the unwanted selenium species form in about equal portions.

TABLE 1b

Oxidative coupling of 2,4-dimethylphenol
Acidic conditions

| Solvent | T [° C.] | t [h] | pKa | Pummerer ketone [%] | Biphenol [%] | Selenium species [%] |
|---|---|---|---|---|---|---|
| Acetic acid* | 85 | 5 | 4.8 | 4.5 | 74.8 | 1.98 |
| Acetic acid* | 60 | 1.5 | 4.8 | 1.8 | 39.8 | 8.0 |
| Trifluoroacetic acid/acetic acid* (3:1) | 85 | 5 | 0.23/4.8 | 2.5 | 77.8 | 1.4 |
| Formic acid* | 60 | 2 | 3.8 | 1.8 | 85.4 | — |
| Methanesulphonic acid | 85 | 5 | −2.6 | — | 3.9 | 6.1 |
| p-Toluene-sulphonic acid | 85 | 5 | −2.8 | — | 15.0 | — |

It can be inferred from Table 1b that, under the acidic conditions according to the invention, it was possible to prepare each biphenol in a very good yield. Using methanesulphonic acid (pKa −2.6) and p-toluenesulphonic acid (pKa −2.8), each having pKa values below the value of 0.0, it was possible to obtain the desired biphenol only in very low yields.

TABLE 2a

Oxidative coupling of 2,4-di-tert-butylphenol
Basic conditions

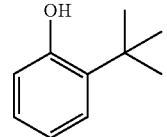

| Solvent | T [° C.] | t [h] | pKb | Biphenol [%] | Selenium species [%] |
|---|---|---|---|---|---|
| Pyridine | 40 | 24 | 8.9 | 20.6 | 46.8 |
| Pyridine | 60 | 7 | 8.9 | 10.1 | 30.4 |

Under basic conditions, the selenium species again forms as the main product of the reaction.

TABLE 2b

Oxidative coupling of 2,4-di-tert-butylphenol
Acidic conditions

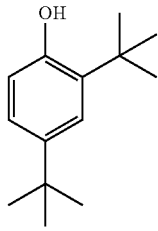

| Solvent | T [° C.] | t [h] | pKa | Biphenol [%] | Selenium species [%] |
|---|---|---|---|---|---|
| Acetic acid* | 50 | 18 | 4.8 | 29.5 | 25.2 |
| Acetic acid* | 85 | 1 | 4.8 | 25.9 | 23.1 |
| Acetic acid* | 105 | 0.2 | 4.8 | 75.1 | 2.6 |
| Formic acid* | 70 | 1 | 3.8 | 46.9 | 7.6 |

Under the acidic conditions according to the invention, the desired biphenol is the main product of the reaction.

TABLE 3a

Oxidative coupling of 2-tert-butyl-4-methylphenol
Basic conditions

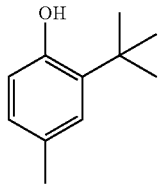

| Solvent | T [° C.] | t [h] | pKb | Biphenol [%] | Selenium species [%] |
|---|---|---|---|---|---|
| Pyridine | 40 | 24 | 8.9 | 7.2 | 61.5 |
| Pyridine | 60 | 7 | 8.9 | 1.6 | 32.2 |
| Pyridine | 85 | 1.5 | 8.9 | 6.1 | 32.5 |
| Pyridine | 100 | 0.5 | 8.9 | 4.5 | 28.9 |

It is again clear from Table 3a too that basic conditions lead to the selenium species, and the desired biphenol is obtained only in very small proportions.

TABLE 3b

Oxidative coupling of 2-tert-butyl-4-methylphenol
Acidic conditions

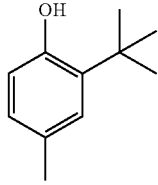

| Solvent | T [° C.] | t [h] | pKa | Biphenol [%] | Selenium species [%] |
|---|---|---|---|---|---|
| Acetic acid* | 50 | 18 | 4.8 | 34.2 | 19.8 |
| Acetic acid* | 85 | 1.5 | 4.8 | 63.7 | 4.0 |
| Acetic acid* | 100 | 0.4 | 4.8 | 53.2 | 2.1 |

Under conditions according to the invention, in contrast the desired biphenol can be prepared in very good yields.

The results summarized in Tables 1a to 3b show clearly that the process according to the invention fulfils the objective defined above. The process according to the invention is a synthesis route by which 2,2'-biphenols can be prepared selectively, in a good yield. In addition, the process according to the invention can also be implemented on the industrial scale.

Further comparative tests are described hereinafter.
2,4-Dimethylphenol was reacted with $SeO_2$.

TABLE 4

Overview of the reaction of 2,4-dimethylphenol with selenium dioxide with various temperatures and solvents after 18 hours. 1.3 equivalents of selenium dioxide (based on 2,4-dimethylphenol) were used in each case.

| Solvent | T [° C.] | t [h] | 2,4-Dimethyl phenol | Pummerer ketone | Biphenol | Selenium species |
|---|---|---|---|---|---|---|
| THF | 90 | 18 | 98 | 1 | 1 | — |
| Glyme | 96 | 18 | — | 17 | 74 | — |
| Glyme | 75 | 18 | 13 | 9 | 52 | 10 |
| Diglyme | 96 | 18 | 95 | 1 | 4 | — |

If glyme (ethylene glycol dimethyl ether) is used as solvent, the biphenol is obtained as the main product here too. However, high temperatures and long reaction times are required, which makes the reaction unattractive for industrial scale use. A further disadvantage is that it is necessary to use the selenium dioxide in superstoichiometric amounts, i.e. in more than 1.0 equivalent. Furthermore, the sum total of the by-products (Pummerer ketone+selenium species) is above 15% in each case. The high proportion of secondary components makes the corresponding workup to obtain the pure substance much more difficult and hence also costlier, which is disadvantageous for an industrial scale process.

With tetrahydrofuran (THF) (pKb 11.5) as solvent, hardly any biphenol forms.

Using the process according to the invention, much better reaction results can be achieved in a much shorter time.

German patent application 102014209967.6 filed May 26, 2015, is incorporated herein by reference.

Numerous modifications and variations on the present invention are possible in light of the above teachings. It is therefore to be understood that within the scope of the appended claims, the invention may be practiced otherwise than as specifically described herein.

The invention claimed is:

1. A process for preparing a 2,2'-biphenol, comprising:
   a) adding a first phenol to a reaction mixture,
   b) adding a second phenol to the reaction mixture,
   c) adding selenium dioxide to the reaction mixture,
   d) adding an acid having a pKa in the range from 0.0 to 5.0 to the reaction mixture, and
   e) heating the reaction mixture such that the first phenol and the second phenol are converted to said 2,2'-biphenol.

2. The process according to claim 1, wherein the first phenol in process step a) is a compound of the general formula I:

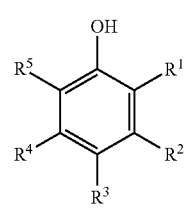

wherein R¹, R², R³, R⁴, R⁵ are each independently selected from the group consisting of:
—H, —(C₁-C₁₂)-alkyl, —O—(C₁-C₁₂)-alkyl-, —(C₆-C₂₀)-aryl, —O—(C₆-C₂₀)-aryl, -halogen, and —OC=O—(C₁-C₁₂)-alkyl,
wherein two adjacent radicals are optionally joined to one another to form a condensed system,
wherein the alkyl and aryl groups mentioned are optionally substituted, and
wherein at least R¹ or R⁵ is —H.

3. The process according to claim 2, wherein R¹, R², R³, R⁴, R⁵ are each independently selected from the group consisting of:
—H—, —(C₁-C₁₂)-alkyl, —O—(C₁-C₁₂)-alkyl, —(C₆-C₂₀)-aryl, and —O—(C₆-C₂₀)-aryl,
wherein the alkyl and aryl groups mentioned are optionally substituted, and
wherein at least R' or R⁵ is —H.

4. The process according to claim 2, wherein R¹, R³, R⁵ are each independently selected from the group consisting of:
—H, and —(C₁-C₁₂)-alkyl,
wherein the alkyl groups mentioned are optionally substituted, and
wherein at least R¹ or R⁵ is —H.

5. The process according to claim 1, wherein the second phenol in process step b) is a compound of the general formula II:

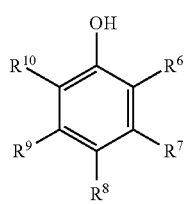

wherein R⁶, R⁷, R⁸, R⁹, R¹⁰ are each independently selected from the group consisting of:
—H, —(C₁-C₁₂)-alkyl-, —O—(C₁-C₁₂)-alkyl-, —(C₆-C₂₀)-aryl, —O—(C₆-C₂₀)-aryl, -halogen, and —OC=O—(C₁-C₁₂)-alkyl,
wherein two adjacent radicals are optionally joined to one another to form a condensed system,
wherein the alkyl and aryl groups mentioned are optionally substituted, and
wherein at least R⁶ or R¹⁰ is —H.

6. The process according to claim 5, wherein R⁶, R⁷, R⁸, R⁹, R¹⁰ are each independently selected from the group consisting of:
—H—, —(C₁-C₁₂)-alkyl, —O—(C₁-C₁₂)-alkyl-, —(C₆-C₂₀)-aryl, and —O—(C₆-C₂₀)-aryl,
wherein the alkyl and aryl groups mentioned are optionally substituted, and
wherein at least R⁶ or R¹⁰ is —H.

7. The process according to claim 5, wherein R⁶, R⁸, R¹⁰ are each independently selected from the group consisting of:
—H, and —(C₁-C₁₂)-alkyl,
wherein the alkyl groups mentioned are optionally substituted, and
wherein at least R⁶ or R¹⁰ is —H.

8. The process according to claim 1, wherein the first phenol is the same as the second phenol.

9. The process according to claim 1, wherein the selenium dioxide is added in process step c) in a molar ratio of from 0.25 to 1.2 based on a total sum of the first and second phenols.

10. The process according to claim 1, wherein the acid in process step d) is selected from the group consisting of: acetic acid, formic acid, trifluoroacetic acid, propionic acid, and phosphoric acid.

11. The process according to claim 1, wherein the acid is used as solvent in process step d).

12. The process according to claim 1, wherein the reaction mixture is heated in process step e) to a temperature in the range from 50° C. to 110° C.

13. The process according to claim 1, wherein the heating in process step e) is effected over a period in the range from 5 minutes to 24 hours.

14. The process according to claim 1, wherein said bisphenol is selected from the group consisting of
3,3',5,5'-tetramethylbiphenyl-2,2'-diol

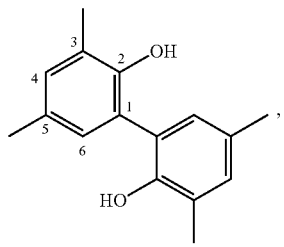

3,3'-di-tert-butyl,5,5'-dimethylbiphenyl-2,2'-diol

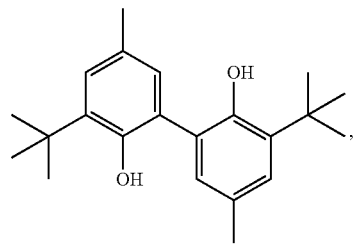 [SMILES: Cc1cc(-c2cc(C)cc(C(C)(C)C)c2O)c(O)c(C(C)(C)C)c1]

3,3',5,5'-tetra-tert-butylbiphenyl-2,2'-diol

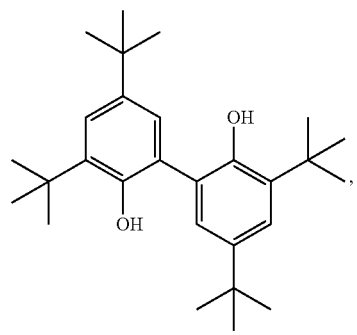 [SMILES: CC(C)(C)c1cc(-c2cc(C(C)(C)C)cc(C(C)(C)C)c2O)c(O)c(C(C)(C)C)c1]

3,3'-diisopropyl-5,5',6,6'-tetramethyl-2,2'-biphenol

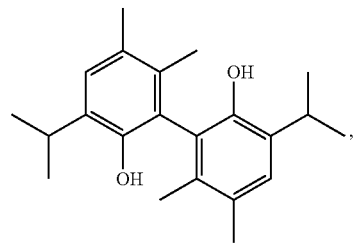 [SMILES: Cc1cc(C(C)C)c(O)c(-c2c(C)c(C)cc(C(C)C)c2O)c1C]

3,3'-di-tert-butyl-5,5',6,6'-tetramethyl-2,2'-biphenol
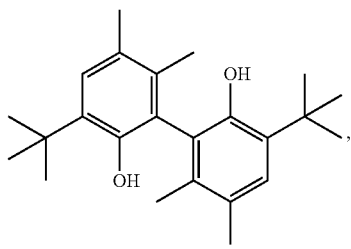 [SMILES: Cc1cc(C(C)(C)C)c(O)c(-c2c(C)c(C)cc(C(C)(C)C)c2O)c1C]
and
3,3',5,5',6,6'-hexamethyl-2,2'-biphenol
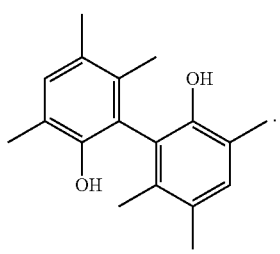
* * * * *